United States Patent [19]

Murata et al.

[11] 4,357,426
[45] Nov. 2, 1982

[54] HUMIDITY SENSITIVE CERAMICS

[75] Inventors: Michihiro Murata, Kyoto; Shinsei Okabe, Takatsuki, both of Japan

[73] Assignee: Murata Manufacturing Co., Ltd., Kyoto, Japan

[21] Appl. No.: 332,096

[22] Filed: Dec. 17, 1981

[30] Foreign Application Priority Data

Dec. 22, 1980 [JP] Japan .............................. 55/182381

[51] Int. Cl.³ ........................................... C04B 35/50
[52] U.S. Cl. ................................... 501/135; 501/136; 501/137; 501/138; 501/139; 501/152; 252/520; 252/521
[58] Field of Search ................................ 501/135–139, 501/152; 252/520, 521

[56] References Cited

U.S. PATENT DOCUMENTS 3,926,858 12/1975 Ichinose et al. ...................... 252/520
4,014,822  3/1977 Fujikawa ............................ 252/521
4,015,230  3/1977 Nitta et al. .......................... 252/521
4,045,375  8/1977 Komatu ............................. 501/152
4,296,608 10/1981 Lawless ............................. 501/152

Primary Examiner—James Poer
Attorney, Agent, or Firm—Birch, Stewart, Kolasch & Birch

[57] ABSTRACT

A humidity sensitive ceramics comprises a sintered body consisting essentially of a semiconductive compound oxide with a perovskite structure and a compound oxide, said semiconductive compound oxide having a composition expressed by the general formula (I):

$$A_{1-x}A'_xBO_{3-\delta} \ldots \quad (I)$$

wherein A is at least one element selected from the group consisting of rare earth elements with atomic numbers 57 to 71, yttrium and hafnium, A' is at least one element selected from the group consisting of alkaline-earth metals, B is at least one element selected from the group consisting of transition elements with atomic numbers 23 to 30, x is a mole fraction and takes a value of the following range, $0 \leq x \leq 1$, and $\delta$ is a non-stoichiometric parameter, said compound oxide having a composition expressed by the general formula (II):

$$AMO_3 \ldots \quad (II)$$

wherein A is at least one element selected from the group consisting of alkaline earth elements, Zn, Cd, Fe, Co, Ni, Mn and Pb, M is at least one element selected from the group consisting of Ti, Zr, Hf and Sn.

1 Claim, 4 Drawing Figures

HUMIDITY SENSITIVE CERAMICS

FIELD OF THE INVENTION

This invention relates to humidity sensitive ceramics which possess the change of resistivity with change in humidity.

BACKGROUND OF THE INVENTION

As a humidity sensor or a moisture detecting element that makes use of the change of resistivity of a humidity sensitive material with change in humidity, there have been used those comprising lithium chloride, or these comprising ceramics of the system such as $TiO_2$-$SnO_2$, $TiO_2$-$V_2O_5$, $MgCr_2O_4$ or $ZnO$-$Li_2O$-$V_2O_5$. Among them, the humidity sensors comprising the above ceramics, or humidity sensitive ceramic sensors possess excellent stability in characteristics as compared with the sensors of lithium chloride. The ceramic sensors possess poor aging in the humidity detecting function as well as the sensors of lithium chloride. For example, when the ceramic sensors of the prior art are allowed to stand 3 months in an atmosphere of 40% relative humidity, the resistance thereof change by some 40% from the value of initial resistance. However, their function can be recovered to the previous level by heating since the ceramics used as a material for humidity sensors do not change in quality even if heated to high temperatures. For this reason, the ceramic sensors are combined with heating element for practical purposes to recover its humidity detecting function by intermittent heating. However, this lead to increase of the consumption of electric power.

SUMMARY OF THE INVENTION

It is therefore an object of the present invention to provide a humidity sensitive ceramics with good aging in the humidity detecting function.

Another object of the present invention is to provide humidity sensitive ceramics which makes it possible to produce humidity sensors with a desired resistance change rate by the variation of compositioned proportions of the components, and the resistance of which is lowered with increase of the humidity.

According to the present invention, there is provided a humidity sensitive ceramics comprising a sintered body consisting essentially of a semiconductive compound oxide with a perovskite structure and a compound oxide. The semiconductive compound oxide has a composition expressed by the general formula(I):

$$A_{1-x}A'_xBO_{3-\delta} \ldots \quad (I)$$

wherein A is at least one element selected from the group consisting of rare earth elements with atomic numbers 57 to 71, yttrium and hafnium, A' is at least one element selected from the group consisting of alkaline-earth metals, B is at least one element selected from the group consisting of transition elements with atomic numbers 23 to 30, x is a mole fraction and takes a value in the following range, $0 \leq x \leq 1$, and $\delta$ is a nonstoichiometric parameter. The compound oxide has a composition expressed by the general formula(II):

$$AMO_3 \ldots \quad (II)$$

wherein A is at least one element selected from the group consisting of alkaline-earth elements, Zn, Cd, Fe, Co, Ni, Mn and Pb, M is at least one element selected from the group consisting of Ti, Zr, Hf and Sn.

In the preferred embodiment, the semiconductive compound oxide having the perovskite structure expressed by the general formula(I): $A_{1-x}A'_xBO_{3-\delta}$, wherein A is at least one element selected from the group consisting of rare-earth elements with atomic numbers 57 to 71 inclusive, yttrium and hafnium, A' is at least one element selected from the group consisting of alkaline-earth metal, and B is at least one element selected from the group consisting of transition elements with atomic numbers 23 to 30 inclusive, may have a composition expressed by the formula: $La_{1-x}Sr_xCo_{1-y}Ni_yO_3$ wherein $0 \leq x \leq 1$ and $0 \leq y \leq 1$.

In further preferred embodiment, the semiconductive compound oxide expressed by the general formula(I) has a composition expressed by the formula: $Nd_{1-x-x'}Sr_xBa_{x'}CoO_3$ wherein $0 \leq x \leq 1$, $0 \leq x' \leq 1$, $0 \leq x+x' \leq 1$.

In another preferred embodiment, the semiconductive compound oxide expressed by the general formula(I) has a composition expressed by the formula: $Y_{1-x}Sr_xCoO_3$, wherein $0 \leq x \leq 1$.

In still another preferred embodiment, the semiconductive compound oxide expressed by the general formula(I) has a composition expressed by the formula: $La_{1-x}Sr_xMnO_3$ wherein $0 \leq x \leq 1$.

In the above general formula(I), A and A' may take a coexistence state, and are also allowed to be exsisted independently each other. Thus, x in the formula may take any value within the range of 0 to 1 inclusive.

In the general formula(I), $A_{1-x}A'_xBO_{3-\delta}$, oxygen defects which changes the composition into a semiconducting state are expressed by using $\delta$ as a nonstoichiometric parameter. The oxygen defect state of the composition can be obtained by sintering the composition in a reducing or oxydizing atmosphere.

In the preferred embodiments, the compound oxide expressed by the general formula(II): $AMO_3$, wherein A is at least one element selected from the group consisting of alkaline-earth metals, Zn, Cd, Fe, Co, Ni, Mn and Pb, and M is at least one element selected from the group consisting of Ti, Zr, Hf and Sn, has a composition $SrTiO_3$, $BaTiO_3$, $CaSnO_3$, or $Sr_{1-y}Ca_yTiO_3$ (where $0 \leq y \leq 1$).

The semiconductive compound oxide with the perovskite structure expressed by the general formula(I) and the compound oxide expressed by the general formula(II) may be mixed in any ratio to produce ceramics with a desired initial resistance and a change rate of resistance with the change in humidity. The semiconductive compound oxide and the compound oxide are generally mixed in the ratio within the range of 1:100 to 100:1, preferably, within the range of 1:50 to 1:1. Because, if humidity sensitive ceramics are composed of the compound oxide $AMO_3$ alone, i.e., if no semiconductive compound oxide with the perovskite structure is present in the ceramics, they possess extremely high resistance, thus making it impossible to put them into practical use. Further, if ceramics are composed of the semiconductive compound oxide with the perovskite structure alone, i.e., if no compound oxide expressed by the general formula(II) is present in the ceramics, they possess considerably small change rate of resistance with change in humidity, thus making it impossible to use them as a material for humidity sensitive sensors.

The humidity sensitive ceramics according to the present invention may be produced in a manner conventionally employed for known ceramic materials. For example, the humidity sensitive ceramics of the present invention may be produced in the following manner:

The raw materials in forms of oxides and/or carbonates are weighed out, mixed, calcined, powdered and granulated with a suitable amount of binder, and the resultant mixture is formed into suitable shapes. The shaped bodies are sintered at a temperature within the range of 800° to 1400° C. to produce humidity sensitive ceramics. The resultant sintered ceramic bodies may be provided with electrodes to produce humidity sensors. The sintered body may be in the shape of disc, rod bar, pellet, or cylindrical. The electrodes for detecting the change of resistivity of ceramics may be formed in any shape, for example, such as opposed, plate electrodes, comb-shaped electrodes, or porous electrodes.

In order to obtain good humidity detecting characteristic, the sintered ceramic body has preferably porosity within the range of 20 to 50%.

In the foregoing, the nonstoichiometric amount of oxygen ($\delta$) in the semiconductive compound oxide with the perovskite structure is not specified but represented in the form of $O_3$ as well as in Examples.

The humidity sensitive ceramics according to the present invention are considerably small in aging even if they are exposed to repeated change of humidity surroundings for a long time, thus making it possible to produce humidity sensors without combining them with heating elements. In addition, the humidity sensitive ceramics with a desired change rate of resistance with change in humidity can be produced at will by variation of compositional ratio of the semiconductive compound oxide and the compound oxide expressed by the general formula $AMO_3$, thus making it possible to produce humidity sensitive sensors with various humidity detecting characteristics.

The invention will be further apparent from the following description with reference to examples and the accompanying drawings.

EXAMPLE 1

As raw materials, there are provided powder of $La_2O_3$, $SrCO_3$, $Co_2O_3$ and $TiO_2$. These raw materials are mixed to obtain mixtures respectively corresponding to a composition $La_{0.8}Sr_{0.2}CoO_3$ or a composition $SrTiO_3$. The resultant mixtures are then calcined at 1100° C., crushed and ground to powder. The resultant presintered powder of $La_{0.8}Sr_{0.2}CoO_3$ and that of $SrTiO_3$ are mixed in various ratios shown in Table 1, granulated by using 10 wt% of binder, and then shaped into disks with a 10 mm diameter and a 0.6 mm thick. The disks are fired in air at 1250° C. to obtain sinterd bodies of ceramics which are humidity sensitive ceramics. A set of porous electrodes of various electrically conductive materials shown in Table 1 are applied to the opposite disk surfaces of the sintered bodies, and a pair of lead wires are connected to the respective electrodes to provide humidity sensors. The porous electrodes may be formed by printing an electrically conductive paste on the opposite disk surfaces of each sintered body, and then stoving the same in air.

Figure 1:
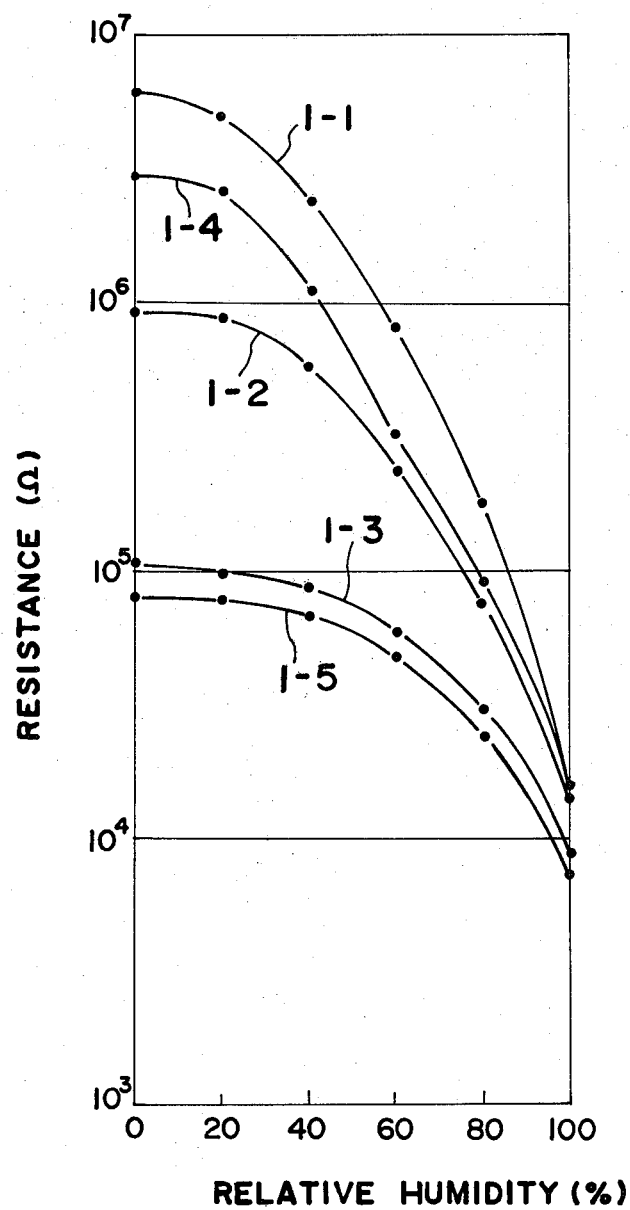
FIGS. 1 to 4 are graphs showing resistance vs. relative humidity characteristics of humidity sensors comprising humidity sensitive ceramics according to the present invention.

For each thus prepared humidity sensor, the resistance at various relative humidities are measured to know the change of restistance with change in humidity. The results are shown in FIG. 1.

TABLE 1

| Specimen No. | Composition (weight %) $La_{0.8}Sr_{0.2}CoO_3$ | $SrTiO_3$ | Electrode Material |
|---|---|---|---|
| 1-1 | 5 | 95 | Au |
| 1-2 | 10 | 90 | Au |
| 1-3 | 15 | 85 | Au |
| 1-4 | 15 | 85 | $RuO_2$ |
| 1-5 | 20 | 80 | Au |

In order to investigate the aging characteristic, the sensors of the specimen No. 1-2 are kept in an atmosphere of 40% or 80% relative humidity, and their resistance are measured after the lapse of 3 and 6 months. Results are shown in Table 1B together with the initial values.

TABLE 1B

| Relative Humidity | Initial value | After 3 months | After 6 months |
|---|---|---|---|
| 40% | 540 KΩ | 560 KΩ | 550 KΩ |
| 80% | 80 KΩ | 80 KΩ | 83 KΩ |

EXAMPLE 2

Using $La_2O_3$, $SrCO_3$, $Co_2O_3$, $TiO_2$, $CaCO_3$, $ZrO_2$ and $MgO$ as raw materials, there are prepared powder of a presintered semiconductive compound oxide, $La_{0.8}Sr_{0.2}CoO_3$, and powder of presintered compound oxides, $CaZrO_3$ and $MgTiO_3$, which are then mixed in the proportions shown in Table 2. The respective resultant mixtures are granulated, shaped and fired in the same manner as in Example 1 to obtain ceramic sintered bodies. A set of porous electrodes are applied to the opposite disk surfaces of each ceramic sintered body by printing a gold paste and then stoving the same in air. A pair of lead wires are electrically connected to the porous gold electrodes.

Figure 2:
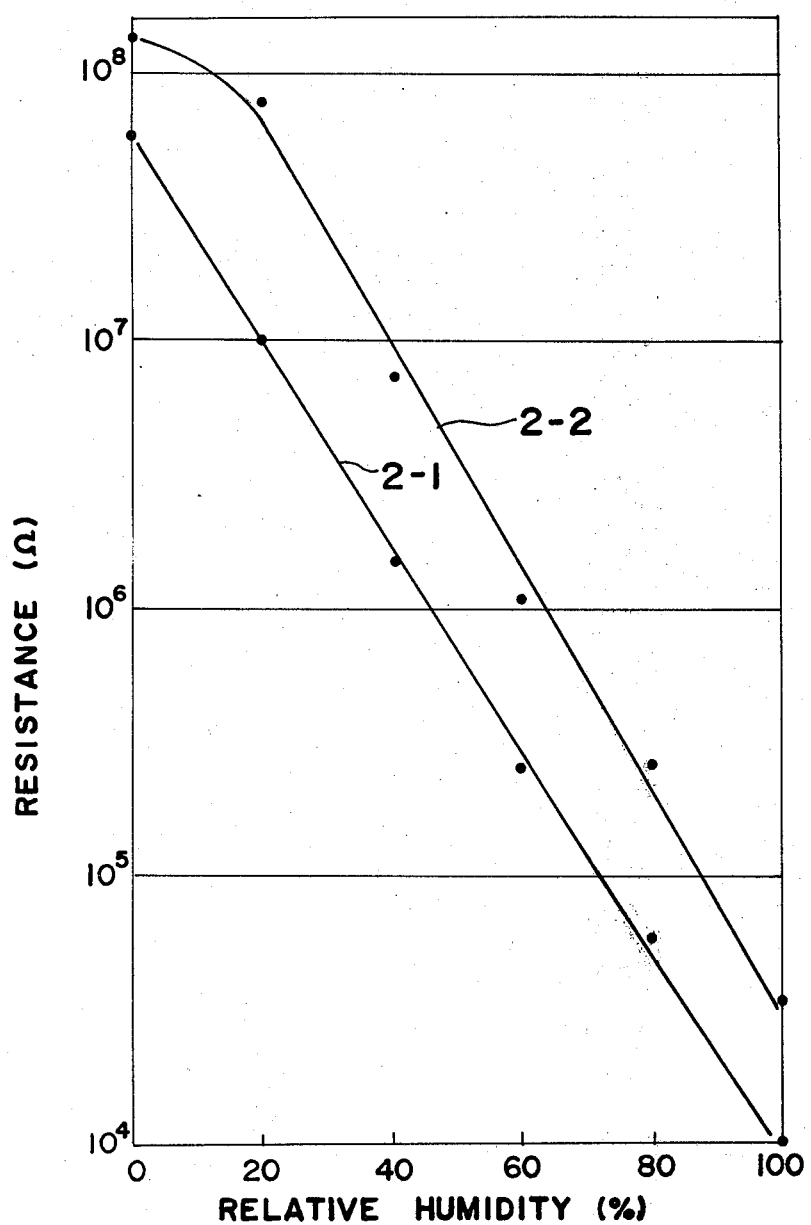

For the thus prepared humidity sensors, the resistance at various relative humidities are measured to know the change of resistance with change in humidity. The results are shown in FIG. 2.

TABLE 2

| Specimen No. | Composition (weight %) $La_{0.8}Sr_{0.2}CoO_3$ | $AMO_3$ |
|---|---|---|
| 2-1 | 25 | $MgTiO_3$: 75 |
| 2-2 | 30 | $CaZrO_3$: 70 |

In order to investigate the aging characteristic, the sensors of the specimen No. 2-2 are kept in an atmosphere of 40% or 80% relative humidity, and their resistance are measured after the lapse of 3 and 6 months. Results are shown in Table 2B together with the initial values.

TABLE 2B

| Relative Humidity | Initial value | After 3 months | After 6 months |
|---|---|---|---|
| 40% | 8 MΩ | 8.3 MΩ | 8.6 MΩ |
| 80% | 280 KΩ | 290 KΩ | 300 KΩ |

EXAMPLE 3

Using $La_2O_3$, $SrCO_3$, $Co_2O_3$, BaO, $TiO_2$, $CaCO_3$ and $SnO_2$ as raw materials, there are prepared mixtures corresponding to a semiconductive compound oxide, $La_{0.8}Sr_{0.2}CoO_3$, and compound oxides, $BaTiO_3$ and $CaSnO_3$. The mixtures are calcined at 1100° C., crushed and powdered.

The resultant powder of $La_{0.8}Sr_{0.2}CoO_3$, that of $BaTiO_3$ and that of $CaSnO_3$ are mixed in the proportions shown in Table 3, together with 10% by weight of a binder, granulated and then shaped into disks with a 10 mm diameter and a 0.5 mm thick. The disks are fired at 1300° C. in air to obtain sintered ceramic bodies. A set of porous gold electrodes are added to the opposite disk surfaces of the sintered bodies in the same manner as in Example 2, and a pair of lead wires are electrically connected to the electrodes.

Figure 3:
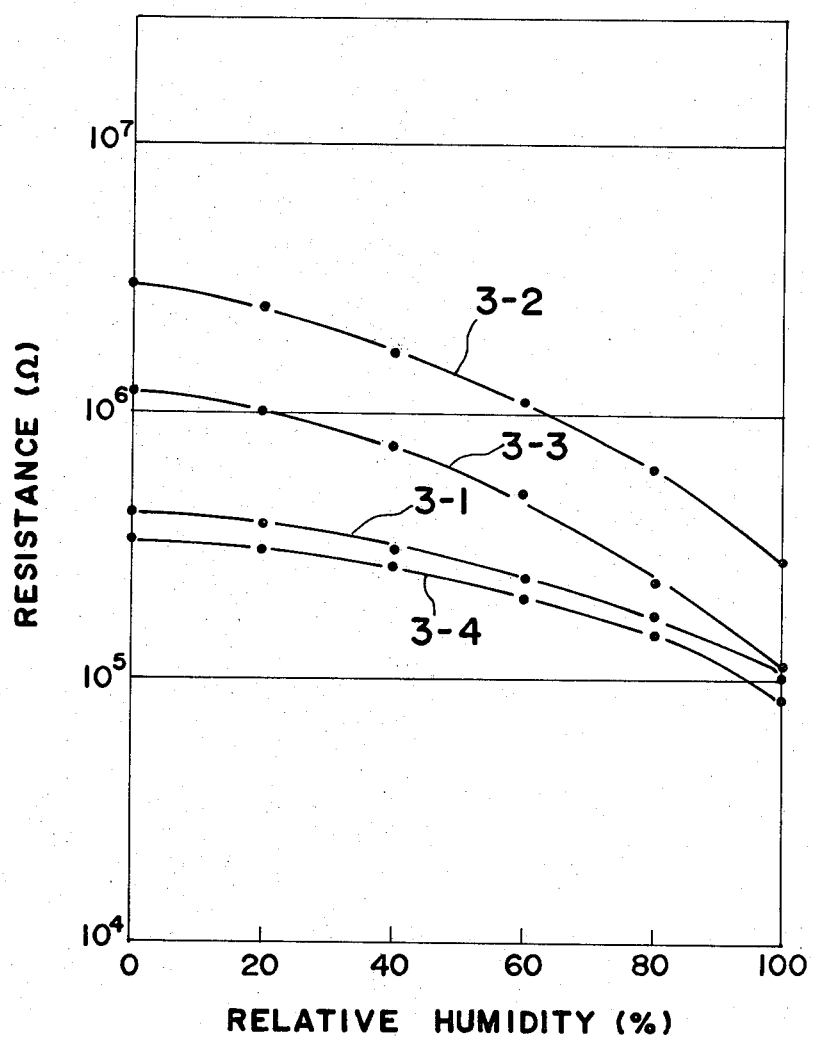

For the thus prepared humidity sensors, the resistance at various relative humidities are measured to know the change of resistance with change in relative humidity. The results are shown in FIG. 3.

TABLE 3

| Specimen No. | Composition (weight %) | |
|---|---|---|
| | $La_{0.8}Sr_{0.2}CoO_3$ | $AMO_3$ |
| 3-1 | 5.0 | $BaTiO_3$: 95.0 |
| 3-2 | 7.5 | $CaSnO_3$: 92.5 |
| 3-3 | 17.5 | $CaSnO_3$: 82.5 |
| 3-4 | 27.5 | $CaSnO_3$: 72.5 |

In order to investigate the aging characteristic, the sensors of the specimen No. 3-1 are kept in an atmosphere of 40% or 80% relative humidity, and their resistance are measured after the lapse of 3 and 6 months. Results are shown in TABLE 3B together with the initial values.

TABLE 3B

| Relative Humidity | Initial value | After 3 months | After 6 months |
|---|---|---|---|
| 40% | 340 KΩ | 345 KΩ | 350 KΩ |
| 80% | 180 KΩ | 182 KΩ | 183 KΩ |

EXAMPLE 4

Raw materials are mixed and calcined at 1100° C. to provide presintered bodies of semiconductive compound oxides and compound oxides respectively having the compositions shown in Table 4. The presintered bodies are crushed, powdered and mixed in the proportions shown in Table 4. The mixed powder is added 10% by weight of binder, granulated and shaped into disks with a 10 mm diameter and a 0.5 mm thick. The disks are then fired at 1250° C. in air to provide sintered ceramic bodies. Porous gold electrodes are applied to the opposite disk surfaces of the sintered bodies in the same manner as in Example 2 and lead wires are connected to the electrodes.

Figure 4:
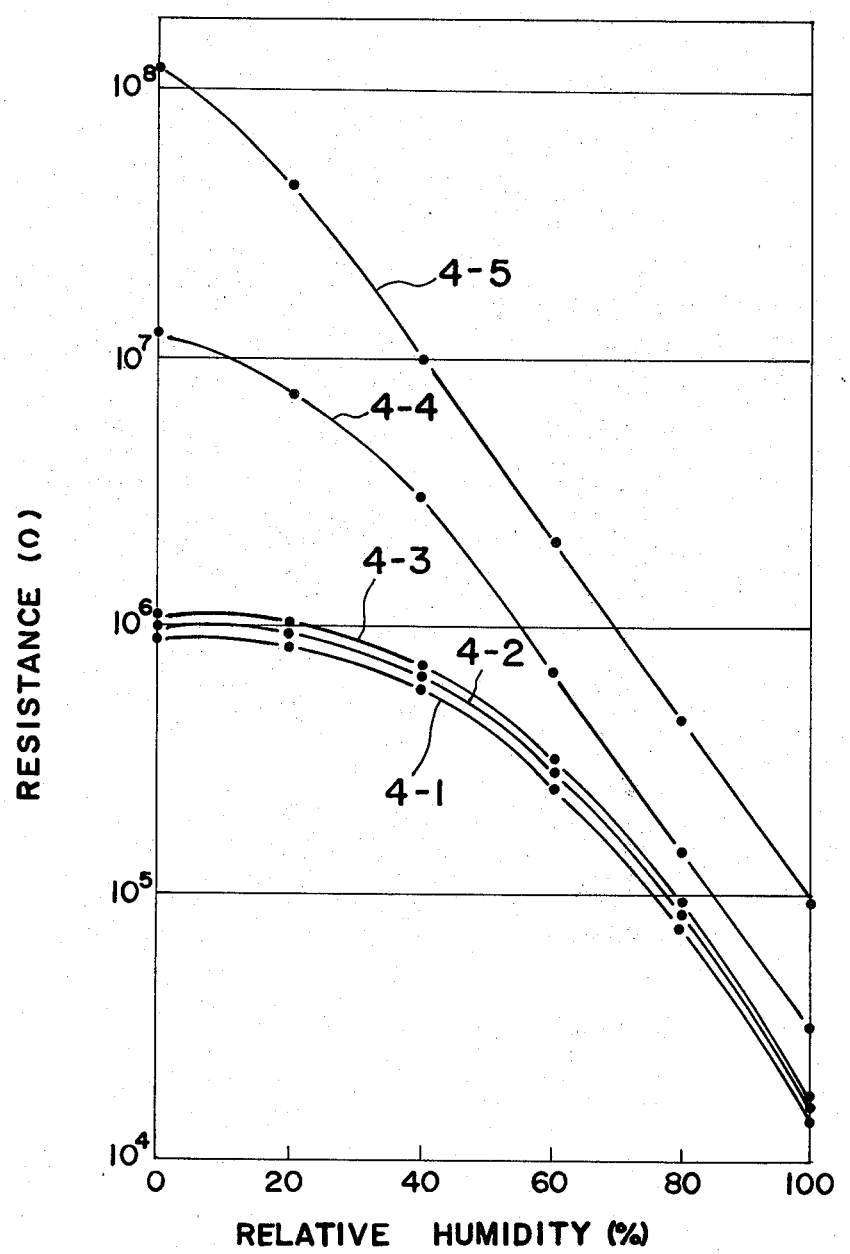

For the thus prepared humidity sensors, the resistance at various relative humidities are measured to know the change of resistance of the sensors with change in humidity. The results are shown in FIG. 4.

TABLE 4

| Specimen No. | Composition (weight %) | |
|---|---|---|
| | $A_{1-x}A'_xBO_3$ | $AMO_3$ |
| 4-1 | $La_{0.8}Sr_{0.2}Co_{0.9}Ni_{0.1}O_3$: 10 | $Sr_{0.95}Ca_{0.05}TiO_3$: 90 |
| 4-2 | $Nd_{0.6}Sr_{0.4}CoO_3$: 10 | $SrTiO_3$: 90 |
| 4-3 | $Nd_{.08}Sr_{0.1}Ba_{0.1}CoO_3$: 10 | $SrTiO_3$: 90 |
| 4-4 | $Y_{0.5}Sr_{0.5}CoO_3$: 10 | $SrTiO_3$: 90 |
| 4-5 | $La_{0.7}Sr_{0.3}MnO_3$: 10 | $SrTiO_3$: 90 |

In order to investigate the aging characteristic, the sensors of the specimen No. 4-1 are kept in an atmosphere of 40% or 80% relative humidity, and their resistance are measured after the lapse of 3 and 6 months. Results are shown in TABLE 4B together with the initial values.

TABLE 4B

| Relative Humidity | Initial value | After 3 months | After 6 months |
|---|---|---|---|
| 40% | 560 KΩ | 550 KΩ | 580 KΩ |
| 80% | 78 KΩ | 79 KΩ | 79 KΩ |

As can be seen from the above examples, the present invention makes it possible to produce humidity sensitive ceramics with a desired change rate of resistance with change in humidity, by variation of the components and that of a compositional ratio of the semiconductive compound oxide to the compound oxide. In addition, the ceramics of the present invention is small in aging even if changes of humidity surroundings are repeated. Thus, the humidity sensitive ceramics of the present invention is useful as a material for humidity sensors, and the humidity sensors comprising the ceramics of the invention can be put into practical use without combining it with a heating element.

What we claim is:

1. A humidity sensitive ceramics comprising a sintered body consisting essentially of a semiconductive compound oxide with a perovskite structure and a compound oxide, said semiconductive compound oxide having a composition expressed by the general formula(I):

$$A_{1-x}A'_xBO_{3-\delta} \ldots \quad (I)$$

wherein A is at least one element selected from the group consisting of rare earth elements with atomic numbers 57 to 71, yttrium and hafnium, A' is at least one element selected from the group consisting of alkaline-earth metals, B is at least one element selected from the group consisting of transition elements with atomic numbers 23 to 30, x is a mole fraction and takes a value of the following range, $0 \leq x \leq 1$, and δ is a non-stoichiometric parameter, said compound oxide having a composition expressed by the general formula(II):

$$AMO_3 \ldots \quad (II)$$

wherein A is at least one element selected from the group consisting of alkaline earth elements, Zn, Cd, Fe, Co, Ni, Mn and Pb, M is at least one element selected from the group consisting of Ti, Zr, Hf and Sn.

* * * * *